US010504227B1

(12) United States Patent
Chilamkurhy et al.

(10) Patent No.: US 10,504,227 B1
(45) Date of Patent: Dec. 10, 2019

(54) APPLICATION OF DEEP LEARNING FOR MEDICAL IMAGING EVALUATION

(71) Applicant: Qure.AI Technologies Private Limited, Mumbai (IN)

(72) Inventors: Sasank Chilamkurhy, Mumbai (IN); Rohit Ghosh, Mumbai (IN); Swetha Tanamala, Mumbai (IN); Pooja Rao, Mumbai (IN); Prashant Warier, Mumbai (IN)

(73) Assignee: Qure.AI Technologies Private Limited, Mumbai (IN)

( * ) Notice: Subject to any disclaimer, the term of this patent is extended or adjusted under 35 U.S.C. 154(b) by 0 days.

(21) Appl. No.: 16/546,412

(22) Filed: Aug. 21, 2019

Related U.S. Application Data

(63) Continuation of application No. 16/268,611, filed on Feb. 6, 2019, which is a continuation of application No. PCT/IB2019/050315, filed on Jan. 15, 2019.

(30) Foreign Application Priority Data

Nov. 14, 2018 (IN) .............................. 201821042894

(51) Int. Cl.
| | |
|---|---|
| *G06K 9/00* | (2006.01) |
| *G06T 7/00* | (2017.01) |
| *G06N 3/08* | (2006.01) |
| *G06N 20/00* | (2019.01) |

(52) U.S. Cl.
CPC .......... *G06T 7/0012* (2013.01); *G06N 3/084* (2013.01); *G06N 20/00* (2019.01); *G06T 2207/10081* (2013.01); *G06T 2207/20081* (2013.01); *G06T 2207/20084* (2013.01)

(58) Field of Classification Search
CPC ........................................ G06N 3/02; G06N 3/08; G06N 3/084; G06N 20/00; G06T 7/0012; G06T 3/4046; G06T 2207/30004; G06T 2207/30016; G06T 2207/30032; G06T 2207/30092; G06T 2207/30096; G06T 2207/30101; G06T 2207/20081; G06T 2207/20084
See application file for complete search history.

(56) References Cited

U.S. PATENT DOCUMENTS

2018/0033144 A1    2/2018  Risman et al.

FOREIGN PATENT DOCUMENTS

| WO | 2017210690 | 12/2017 |
|---|---|---|
| WO | 2018009405 | 1/2018 |

OTHER PUBLICATIONS

International search report and written opinion issued in the corresponding PCT application No. PCT/IB2019/050315.
Lancet 2018; 392; 2388-96: Deep learning algorithms for detection of critical findings in head CT scans: a retrospective study. Sasank Chilamkurthy.

*Primary Examiner* — Duy M Dang
(74) *Attorney, Agent, or Firm* — Wiley Rein LLP

(57) ABSTRACT

This disclosure generally pertains to methods and systems for processing electronic data obtained from imaging or other diagnostic and evaluative medical procedures. Certain embodiments relate to methods for the development of deep learning algorithms that perform machine recognition of specific features and conditions in imaging and other medical data. Another embodiment provides systems configured to detect and localize medical abnormalities on medical imaging scans by a deep learning algorithm.

30 Claims, 7 Drawing Sheets

(b) Localization output produced by the calvarial fracture detection algorithm.

(a) Output produced by the hemorrhage segmentation algorithms.

Intracranial hemorrhage

Intraparenchymal hemorrhage

Intraventricular hemorrhage

Subdural hemorrhage

Extradural hemorrhage

Subarachnoid hemorrhage

Calvarial Fracture

Midline Shift

Mass effect

APPLICATION OF DEEP LEARNING FOR MEDICAL IMAGING EVALUATION

RELATED APPLICATIONS

This application is a continuation of the U.S. patent application Ser. No. 16/268,611, filed Feb. 6, 2019, which claims priority benefit of International Patent Application No. PCT/IB2019/050315, filed Jan. 15, 2019, which claims priority benefit of Indian Patent Application No. 201821042894, filed Nov. 14, 2018, which are incorporated entirely by reference herein for all purposes.

TECHNICAL FIELD

This disclosure generally pertains to methods and systems for processing electronic data obtained from imaging or other diagnostic and evaluative medical procedures. Some embodiments relate to methods for the development of deep learning algorithms that perform machine recognition of specific features and conditions in imaging and other medical data.

BACKGROUND ART

Medical imaging techniques, such as computed topography (CT) and X-ray imaging, are widely used in diagnosis, clinical studies and treatment planning. There is an emerging need for automated approaches to improve the efficiency, accuracy and cost effectiveness of the medical imaging evaluation.

Non-contrast head CT scans are among the most commonly used emergency room diagnostic tools for patients with head injury or in those with symptoms suggesting a stroke or rise in intracranial pressure. Their wide availability and relatively low acquisition time makes them a commonly used first-line diagnostic modality. The percentage of annual US emergency room visits that involve a CT scan has been increasing for the last few decades and the use of head CT to exclude the need for neurosurgical intervention is on the rise.

The most critical, time-sensitive abnormalities that can be readily detected on CT scan include intracranial hemorrhages, raised intracranial pressure and cranial fractures. A key evaluation goal in patients with stroke is excluding an intracranial hemorrhage. This depends on CT imaging and its swift interpretation. Similarly, immediate CT scan interpretation is crucial in patients with a suspected acute intracranial hemorrhage to evaluate the need for neurosurgical treatment. Cranial fractures, if open or depressed will usually require urgent neurosurgical intervention. Cranial fractures are also the most commonly missed major abnormality on head CT scans, especially if coursing in an axial plane.

While these abnormalities are found only on a small fraction of CT scans, streamlining the head CT scan interpretation workflow by automating the initial screening and triage process, would significantly decrease the time to diagnosis and expedite treatment. This would in turn decrease morbidity and mortality consequent to stroke and head injury. An automated head CT scan screening and triage system would be valuable for queue management in a busy trauma care setting, or to facilitate decision-making in remote locations without an immediate radiologist availability.

The past year has seen a number of advances in application of deep learning for medical imaging interpretation tasks, with robust evidence that deep learning can perform specific medical imaging tasks including identifying and grading diabetic retinopathy and classifying skin lesions as benign or malignant with accuracy equivalent to specialist physicians. Deep learning algorithms have also been trained to detect abnormalities on radiological images such as chest radiographs, chest CT and head CT through 'classification' algorithms; as well as to localize and quantify disease patterns or anatomical volumes through 'segmentation' algorithms.

The development of an accurate deep learning algorithm for radiology requires, in addition to appropriate model architectures, a large number of accurately labeled scans that will be used to train the algorithm. The chances that the algorithm generalizes well to new settings increase when the training dataset is large and includes scans from diverse sources.

There are several studies on development and validation of Computer aided diagnosis (CAD) algorithms on low volumes of head CT scans. Deep learning has been earlier used to detect intracranial hemorrhages. Traditional computer vision techniques were more common for detection of fractures and midline shift. Training and validation datasets had <200 head CT scans for most studies, raising concerns about the robustness of these algorithms. Furthermore, there were no standard public head CT datasets to directly compare the algorithms' performance.

SUMMARY OF THE INVENTION

The present disclosure describes the development and clinical validation of fully automated deep learning systems that are trained to detect and localize abnormalities from medical imaging scans.

Certain embodiments relate to the development and validation of a deep learning system to detect and localize head CT scan abnormalities. The trained algorithms detect five kinds of intracranial hemorrhages (ICH) namely intraparenchymal (IPH), intraventricular (IVH), subdural (SDH), extradural (EDH) and subarachnoid (SAH), and skull/calvarial/cranial vault fractures with maximized AUC (area under the ROC curve). The trained algorithms also detect mass effect and midline shift, both used as indicators of severity of the brain injury.

In particular, an embodiment provides a method for developing a deep learning system to detect and localize medical abnormalities on head CT scans comprising:

Selecting medical imaging scans and extracting medical abnormalities using natural language processing (NLP) algorithms, wherein each type of the medical abnormalities is annotated at scan, slice and pixel levels;

Training a slice-wise deep learning algorithm comprising a convolutional neural network architecture with the selected medical imaging scans to segment pixel-level annotated scans;

Training the deep learning algorithm comprising a convolutional neural network architecture with the selected medical imaging scans, wherein the architecture is modified by using multiple parallel fully connected layers to generate slice-level confidences;

Predicting confidences for the presence of each type of medical abnormalities, wherein the confidences at the slice-level are combined across slices using a fully connected layer to predict the scan-level confidence for the presence of the medical abnormalities and their types;

Generating a score that corresponds to a level of recognition of the medical abnormalities and outputting a mask representing the precise location and extent of the medical abnormalities; and Validating the accuracy of the deep learning algorithm for detecting the medical abnormalities by comparing with the radiologist reports.

According to an embodiment, the said medical imaging scans include but not limited to CT, X-ray, magnetic resonance imaging (MRI), and ultrasound procedures. For head CT scans, the said medical abnormalities include but not limited to intracranial hemorrhage and each of the 5 types of hemorrhages including intraparenchymal hemorrhage (IPH), intraventricular hemorrhage (IVH), subdural intracranial hemorrhage (SDH), epidural hemorrhage (EDH), and subarachnoid hemorrhage (SAH); midline shift; mass effect; and skull/calvarial fractures.

Further, for a given head CT scan, the scan is preprocessed by windowing to three separate windows, including brain window, bone window and subdural window, and stacking the windows as channels.

Another embodiment provides a system configured to detect and localize medical abnormalities on head CT scans by a deep learning algorithm, wherein the deep learning algorithm is developed by the steps of:

Selecting medical imaging scans and extracting medical abnormalities using natural language processing (NLP) algorithms, wherein each type of the medical abnormalities is annotated at scan, slice and pixel levels;

Training a slice-wise deep learning algorithm comprising a convolutional neural network architecture with the selected medical imaging scans to segment pixel-level annotated scans;

Training the deep learning algorithm comprising a convolutional neural network architecture with the selected medical imaging scans, wherein the architecture is modified by using multiple parallel fully connected layer to generate slice-level confidences;

Predicting confidences for the presence of each type of medical abnormalities, wherein the confidences at the slice-level are combined across slices using a fully connected layer to predict the scan-level confidence for the presence of the medical abnormalities and their types;

Generating a score that corresponds to a level of recognition of the medical abnormalities and outputting a mask representing the precise location and extent of the medical abnormalities; and Validating the accuracy of the deep learning algorithm for detecting the medical abnormalities by comparing with the radiologist reports.

Further, a system configured to detect and localize medical abnormalities on head CT scans by a deep learning algorithm, wherein the algorithm achieves AUCs of 0.94±0.02, 0.96±0.03, 0.93±0.07, 0.95±0.04, 0.97±0.06, and 0.96±0.04 for detecting ICH, IPH, IVH, SDH, EDH and SAH, respectively.

Advantageous Effects of the Invention

The present invention provides deep learning algorithms to separately detect as many as nine critical findings from head CT scans. The said algorithms have been validated on a large dataset versus clinical radiology reports. The said algorithms also have been validated versus consensus of three radiologists on a dataset acquired from a completely different source than that of the development dataset. Further, there is very little literature to date describing the accurate use of deep learning algorithms to detect cranial fractures. The present invention provides deep learning algorithms that are able to perform this task with high accuracy. The clinical validation of algorithms that detect mass effect and midline shift (both used to estimate severity of a variety on intracranial conditions and the need for urgent intervention) on such a large number of patients is also unique. As importantly, the said algorithms can be useful for automated triaging or notification of patients with critical findings as soon as a head CT scan is acquired.

DETAILED DESCRIPTION

Figure 1:
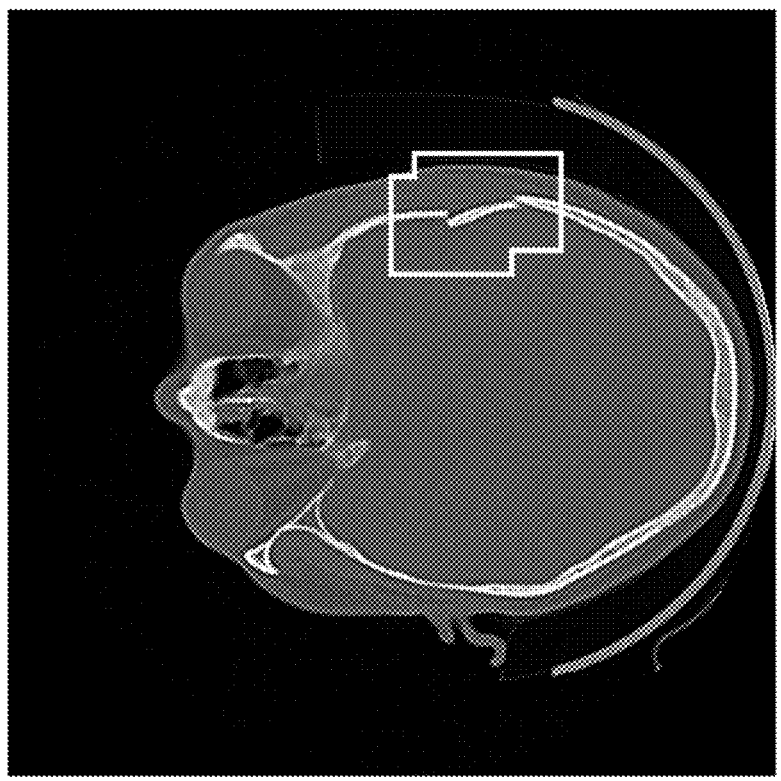
FIG. 1 Localizations produced by the algorithms. These can provide a visual display of the results.
Figure 1:
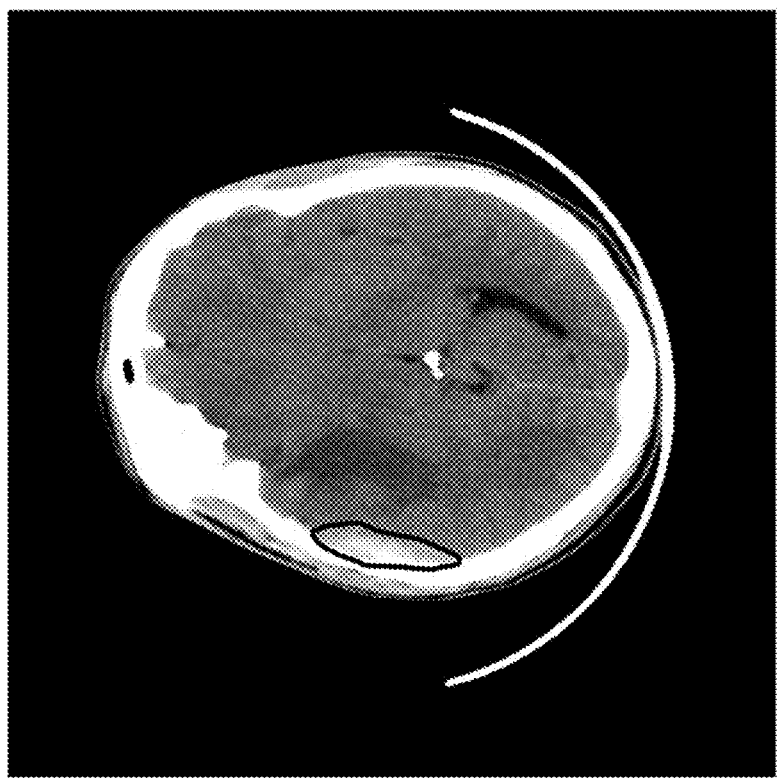

It should be understood that this invention is not limited to the particular methodology, protocols, and systems, etc., described herein and as such may vary. The terminology used herein is for the purpose of describing particular embodiments only, and is not intended to limit the scope of the present invention, which is defined solely by the claims.

As used in the specification and appended claims, unless specified to the contrary, the following terms have the meaning indicated below.

"Architecture" refers to a set of rules and methods that describe the functionality, organization, and implementation of computer systems.

"Convolutional neural network (CNN)" refers to a class of deep, feed-forward artificial neural networks, most commonly applied to analyzing visual imagery. CNNs use a variation of multilayer perceptrons designed to require minimal preprocessing. A CNN consists of an input and an output layer, as well as multiple hidden layers. The hidden layers of a CNN typically consist of convolutional layers, pooling layers, fully connected layers and normalization layers. Convolutional layers apply a convolution operation to the input, passing the result to the next layer. Local or global pooling layers combine the outputs of neuron clusters at one layer into a single neuron in the next layer. Fully connected layers connect every neuron in one layer to every neuron in another layer. CNNs use relatively little pre-processing compared to other image classification algorithms. This means that the network learns the filters that in traditional algorithms were hand-engineered. This independence from prior knowledge and human effort in feature design is a major advantage.

"Heuristics" refers to a technique designed for solving a problem more quickly when classic methods are too slow, or for finding an approximate solution when classic methods fail to find any exact solution. This is achieved by trading optimality, completeness, accuracy, or precision for speed. In a way, it can be considered a shortcut. A heuristic function, also called simply a heuristic, is a function that ranks alternatives in search algorithms at each branching step based on available information to decide which branch to follow. The objective of a heuristic is to produce a solution in a reasonable time frame that is good enough for solving the problem at hand. This solution may not be the best of all the solutions to this problem, or it may simply approximate the exact solution.

"Natural language processing (NLP)" refers to a way for computers to analyze, understand, and derive meaning from human language in a smart and useful way. By utilizing NLP, developers can organize and structure knowledge to perform tasks such as automatic summarization, translation named entity recognition, relationship extraction, sentiment analysis, speech recognition, and topic segmentation.

The present disclosure illustrates various techniques and configurations that enable the integration and use of machine learning analysis in a data-driven image evaluation workflow. For example, machine learning analysis (such as trained models of image detection of certain medical conditions) may be performed upon medical imaging procedure data produced as part of a medical imaging study. The medical imaging procedure data may include image data captured by an imaging modality, and order data (such as data indicating a request for a radiological image read), each produced to facilitate a medical imaging evaluation (such as a radiology read to be performed by a radiologist or a diagnostic evaluation by another qualified medical professional).

For example, the machine learning analysis may receive and process images from medical imaging procedure data, to identify trained structures, conditions, and conditions within images of a particular study. The machine learning analysis may result in the automated detection, indication, or confirmation of certain medical conditions within the images, such as the detection of urgent or life-critical medical conditions, clinically serious abnormalities, and other key findings. Based on the result of the machine learning analysis, the medical evaluation for the images and the associated imaging procedure may be prioritized, or otherwise changed or modified. Further, the detection of the medical conditions may be used to assist the assignment of the medical imaging data to particular evaluators, the evaluation process for the medical imaging data, or implement other actions prior to, or concurrent with, the medical imaging evaluation (or the generation of a data item such as a report from such medical imaging evaluation).

As further discussed herein, the machine learning analysis may be provided on behalf of any number of machine learning algorithms and trained models, including but not limited to deep learning models (also known as deep machine learning, or hierarchical models) that have been trained to perform image recognition tasks, particularly for certain types of medical conditions upon medical images of human anatomy and anatomical representations. As used herein, the term "machine learning" is used to refer to the various classes of artificial intelligence algorithms and algorithm-driven approaches that are capable of performing machine-driven (e.g., computer-aided) identification of trained structures, with the term "deep learning" referring to a multiple-level operation of such machine learning algorithms using multiple levels of representation and abstraction. However, it will be apparent that the role of the machine learning algorithms that are applied, used, and configured in the presently described medical imaging evaluation may be supplemented or substituted by any number of other algorithm-based approaches, including variations of artificial neural networks, learning-capable algorithms, trainable object classifications, and other artificial intelligence processing techniques.

In some of the following examples, reference is made to radiology medical imaging procedures (e.g., computed tomography (CT), magnetic resonance imaging (MRI), Ultrasound, and X-ray procedures, etc.) and diagnostic evaluation of the images produced from such imaging procedures that would be performed with an image evaluation (e.g., radiology read) by a licensed and credentialed radiologist. It will be understood that the applicability of the presently described techniques and systems will extend to a wide variety of imaging data (and other data representations) produced by various medical procedures and specialties, including those not involving traditional radiology imaging modalities. Such specialties include, but are not limited to, pathology, medical photography, medical data measurements such as electroencephalography (EEG) and electrocardiography (EKG) procedures, cardiology data, neuroscience data, preclinical imaging, and other data collection procedures occurring in connection with telemedicine, telepathology, remote diagnostics, and other applications of medical procedures and medical science. Accordingly, the performance of the data recognition and workflow modification techniques described herein may apply to a variety of medical image data types, settings, and use cases, including captured static images and multi-image (e.g. video) representations.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

EXAMPLES

Example 1. Deep Learning Algorithms for Detection of Critical Findings in Head CT Scans 1.1 Datasets 313,318 anonymous head CT scans were retrospectively collected from several centers in India. These centers, which included both in-hospital and outpatient radiology centers, employ a variety of CT scanner models (Table 1) with slices per rotation ranging from 2 to 128. Each of the scans had an electronic clinical report associated with them which we used as the gold standard during the algorithm development process.

TABLE 1

Models of CT scanners used for each dataset.

| Dataset | CT Scanner Models |
|---|---|
| Qure25k & Development | GE BrightSpeed, GE Brivo CT315, GE Brivo CT385, GE HiSpeed, GE LightSpeed, GE ProSpeed, GE Revolution ACTs, Philips Brilliance, Siemens Definition, Siemens Emotion, Siemens Sensation, Siemens SOMATOM, Siemens Spirit |
| CQ500 | GE BrightSpeed, GE Discovery CT750 HD, GE LightSpeed, GE Optima CT660, Philips MX 16-slice, Philips Access-32 CT |

Of these scans, scans of 23,263 randomly chosen patients (Qure25k dataset) were selected for validation and the scans of rest of the patients (development dataset) were used to train/develop the algorithms. Post-operative scans and scans of patients less than years old were removed from the Qure25k dataset. This dataset was not used during the algorithm development process.

A clinical validation dataset (referred as CQ500 dataset) was provided by the Centre for Advanced Research in Imaging, Neurosciences and Genomics (CARING), New Delhi, India. This dataset was a subset of head CT scans taken at various radiology centers in New Delhi. Approximately, half of the centers are stand-alone outpatient centers and the other half are radiology departments embedded in large hospitals. There was no overlap between these centers and the centers from where the development dataset was obtained. CT scanners used at these centers had slices per rotation varying from 16 to 128. Models of the CT scanners are listed in Table 1. The data was pulled from local PACS servers and anonymized in compliance with internally defined HIPAA guidelines. Since both the datasets were retrospectively obtained and fully anonymized, the study was exempted from IRB approval.

Similar to the development and Qure25k datasets, clinical radiology reports associated with the scans in the CQ500 dataset were available. Clinical radiology reports were used for the dataset selection as described below.

The CQ500 dataset were collected in two batches (B1 & B2). Batch B1 was collected by selecting all the head CT scans taken at the above centers for 30 days starting from 20 Nov. 2017. Batch B2 was selected from the rest of the scans in the following way:
1. A natural language processing (NLP) algorithm was used to detect IPH, SDH, EDH, SAH, IVH, calvarial fractures from clinical radiology reports.
2. Reports were then randomly selected so that there are around 80 scans with each of IPH, SDH, EDH, SAH and calvarial fractures.

Each of the selected scans were then screened for the following exclusion criteria:
No post-operative defect
No non-contrast axial series covering complete brain.
Age <7 (estimated from cranial sutures if data is unavailable).

1.2 Reading the Scans

Three senior radiologists served as independent raters for the CT scans in the CQ500 dataset. They had corresponding experience of 8, 12 and 20 years in cranial CT interpretation. None of the three raters was involved in the clinical care or evaluation of the enrolled patients, nor did they have access to clinical history of any of the patients. Each of the radiologists independently evaluated the scans in the CQ500 dataset with the instructions for recording the findings and query resolution. The order of presentation of the scans was randomized so as to minimize the recall of the patients' follow up scans.

Each of the raters recorded the following findings for each scan:
The presence or absence of an intracranial hemorrhage and if present, its type(s) (intra-parenchymal, intraventricular, extradural, subdural and subarachnoid).
The presence or absence of midline shift and mass effect.
The presence or absence of fractures. If present, if it is (partly) a calvarial fracture.

Intra-axial presence of blood due to any etiology such as hemorrhagic contusion, tumor/infarct with hemorrhagic component was also included in the definition of intraparenchymal hemorrhage. Chronic hemorrhages were considered positive in this study. Mass effect was defined as any of the following: local mass effect, ventricular effacement, midline shift and herniation. Midline shift was considered positive if the amount of shift was greater than 5 mm. If there is at least one fracture that extends into the skullcap, the scan is considered to have a calvarial fracture.

If unanimous agreement for each of the findings was not achieved by the three raters, the interpretation of majority of the raters was used as the final diagnosis.

On the development and Qure25k datasets, clinical reports written by radiologists were considered as the gold standard. However, these were written in free text rather than in a structured format. Therefore, a rule based natural language processing (NLP) algorithm was applied on radiologist's clinical reports to automatically infer the findings recorded above. This algorithm was validated on a subset of reports from the Qure25k dataset to ensure that the inferred information was accurate and could be used as gold standard.

1.3. Developing the Deep Learning Algorithms

Deep learning is a form of machine learning where the model used is a neural network with a large number of (usually convolutional) layers. Training this model requires large amount of data for which the truth is already known. Training is usually performed by an algorithm called back propagation. In this algorithm, model is iteratively modified to minimize the error between predictions of the model and the known ground truth for each data point.

One of the main challenges in the development of the algorithms was the three-dimensional (3D) nature of the CT scans. This was primarily due to an issue termed as 'curse of dimensionality' where the data required to train a machine learning algorithm scales exponentially with the dimensionality of data. Deep learning techniques have been extensively researched for the tasks of segmentation and classification of two dimensional images. While the segmentation of 3D images is studied in multiple contexts, their classification is not as well investigated. One closely related problem is recognition of human actions from short video clips (because videos are three-dimensional with the time as the third dimension). Despite that this problem is well explored in the literature, there was no emergence of a leading architecture for this task. The approach of classification is closely related to that of Simonyan and Zisserman (*Advances in neural information processing systems*, pages 568-576, 2014), and involved slice level and pixel level annotation of a large number of scans.

In this study, separate deep learning models were trained for each of the subtasks viz. intracranial bleeds, midline shift/mass effect and calvarial fractures which we describe below.

1.3.1 Intracranial Hemorrhage

Development dataset was searched using natural language processing (NLP) algorithms to select some non-contrast head CT scans which were reported with any of the intraparenchymal hemorrhage (IPH), intraventricular hemorrhage (IVH), subdural intracranial hemorrhage (SDH), epidural hemorrhage (EDH), subarachnoid hemorrhage (SAH) and those with neither of these. Each slice in these scans was manually labeled with the hemorrhages that are visible in that slice. In all, 4304 scans (165809 slices) were annotated, of which number of scans (slices) with IPH, IVH, SDH, EDH, SAH and neither of these were 1787 (12857), 299 (3147), 938 (11709), 623 (5424), 888 (6861) and 944 (133897) respectively.

ResNet18, a popular convolutional neural network architecture with a slight modification was used to predict SoftMax based confidences for the presence of each type of hemorrhage in a slice. The architecture was modified by using five parallel fully connected (FC) layers in place of a single FC layer. This design was based on the assumption that the image features for detecting hemorrhages would be similar for all the hemorrhage types. The confidences at the slice-level are combined using a random forest to predict the scan-level confidence for the presence of intracranial hemorrhage and its types.

An independent model was further trained to localize the following type of hemorrhages: IPH, SDH, EDH. Localization requires dense prediction of presence or absence of bleed for every pixel in the scan. To train models for dense predictions, pixels corresponding to each bleed were annotated for a subset of the above slice-annotated images to provide the ground truth for the model. This set contained 1706 images of which number of images with IPH, SDH, EDH and neither of these are 506, 243, 277 and 750 respectively. A slice-wise 2D UNet7 based architecture was used for segmentation of each type of hemorrhage.

Since segmentation networks for hemorrhage detection algorithms were trained, a mask representing the precise location and extent of the hemorrhage (except for the subarachnoid hemorrhage) was outputted, in addition to detecting its presence. See FIG. 1a.

1.3.2 Midline Shift and Mass Effect

The algorithm for detecting midline shift and mass effect was very similar to the one for detecting intracranial hemorrhage. Each slice from select scans was labeled for the presence or absence of midline shift and mass effect in that slice. Overall, 699 scans (26135 slices) were annotated, of which number of scans (slices) with mass effect were 320 (3143) and midline shift were 249 (2074).

Modified ResNet18 with two parallel fully connected layers was used to predict slice wise confidences for the presence of mass effect and midline shift respectively. These slice level confidences were thereby combined using a random forest to predict scan-level confidences for both the abnormalities.

1.3.3 Calvarial Fractures

Development dataset was searched with NLP algorithm to select some scans with calvarial fractures. Each slice in these scans was annotated by marking a tight bounding box around fractures. Number of scans annotated were 1119 (42942 slices) of which 9938 slices showed a calvarial fracture.

Slices along with target bounding box was fed into a DeepLab based architecture to predict pixel-wise heatmap for fractures (shown in FIG. 1b). Skull fractures are extremely sparse in this representation. Gradient flow in the backpropagation algorithm tends to be hindered for such sparse signals. Therefore, hard negative mining loss was employed to counter the sparsity of the annotation.

Features representative of local fracture lesions and their volumes from the generated heatmaps of the whole scan were engineered. These features were used to train a random forest to predict scan-wise confidence of presence of a calvarial fracture.

1.3.4 Preprocessing

For a given CT scan, the non-contrast axial series which uses soft reconstruction kernel was used and resampled so that slice thickness is around 5 mm. All the slices of this series were resized to a size of 224×224 pixels before passing to our deep learning models. Instead of passing the whole dynamic range of CT densities as a single channel, the densities were windowed by using three separate windows and stacked as channels. Windows used were brain window (l=40, w=80), bone window (l=500, w=3000) and subdural window (l=175, w=50). This was because fracture visible in the bone window could indicate existence of an extra axial bleed in the brain window and conversely, presence of scalp hematoma in the brain window could correlate with a fracture. Subdural window helps differentiate between the skull and an extra axial bleed that might have been indistinguishable in a normal brain window.

1.3.5 Training Details

The annotations were split into train and val sets randomly stratified on patients. Train set was used to train the networks while val set was used to select the hyperparameters. All the weights of network architectures were randomly initialized. During training, the data augmentation strategy used was same as that of He et al. (*Proceedings of the IEEE conference on computer vision and pattern recognition*, pages 770-778, 2016.): random sized crops, horizontal flips and pixel intensity augmentation. Dropout of 0.5 was used after the last two downsampling blocks of the networks. SGD was used with a batch size of 32. Learning rates started from 0.01 and were decayed by 2 every 20 epochs. Weighted cross entropy with weight of 20 for positive class was used as the loss criterion. Final model was selected based on the performance on val set after running for 200 epochs (i.e. early stopping). Training was done on Nvidia Titan X GPUs with PyTorch framework. It took around 15 hours to train each model.

1.3.6 Comparison of Algorithms to Radiologist

Two-sided Fisher's exact tests were used to compare algorithms' performance at high sensitivity operating point to individual radiologist's performance on CQ500 dataset. The null hypotheses were that radiologist and algorithm performed equally well on positive and negative scans respectively. Note that the hypothesis on positive scans implies that sensitivity is same for a radiologist and algorithms. Similarly, for negative scans, it means that specificity is same. Fisher's exact test was chosen because the approximation used in chi-squared test is not valid when the data is very unequally distributed (i.e. sensitivity/specificity≈1). P-values of the tests are tabulated in Table 2.

TABLE 2 p-values for 2-sided test with null hypothesis that algorithms and raters performed equally well on positive and negative scans.

| Finding | Positive Scans | | | Negative Scans | | |
| --- | --- | --- | --- | --- | --- | --- |
| | Rater 1 | Rater 2 | Rater 3 | Rate 1 | Rater 2 | Rater 3 |
| Intracranial hemorrhage | 0.54 | 0.24 | 0.11 | $<10^{-4}$ | $<10^{-4}$ | $<10^{-4}$ |
| Intraparenchymal | 1.00 | 0.17 | 1.00 | $<10^{-4}$ | $<10^{-4}$ | $<10^{-4}$ |
| Intraventricular | 1.00 | 0.42 | 1.00 | $<10^{-4}$ | $<10^{-4}$ | $<10^{-4}$ |
| Subdural | 0.01 | 0.07 | 1.00 | $<10^{-4}$ | $<10^{-4}$ | $<10^{-4}$ |
| Extradural | 1.00 | 1.00 | 0.16 | $<10^{-4}$ | $<10^{-4}$ | $<10^{-4}$ |
| Subarachnoid | 0.11 | 1.00 | 1.00 | $<10^{-4}$ | $<10^{-4}$ | $<10^{-4}$ |
| Calvarial fracture | 1.00 | $<10^{-4}$ | 1.00 | $<10^{-4}$ | $<10^{-4}$ | $<10^{-4}$ |
| Mass Effect | 0.03 | 1.00 | 0.13 | $<10^{-4}$ | $<10^{-4}$ | $<10^{-4}$ |
| Midline shift | 1.00 | 0.03 | 0.36 | 0.73 | $<10^{-4}$ | $<10^{-4}$ |

It can be seen from Table 2, null hypothesis that algorithms' sensitivity is indistinguishable from that of raters cannot be rejected for almost all the findings. For those findings—rater pairs (bolded in the table) with significant difference, further one-sided Fisher's tests found that algorithms have better sensitivity ($p<0·05$). Another inference from Table 2 is that specificities of algorithms and raters are significantly different (except for one pair: mass effect & Rater 1). One-sided tests confirm that specificities of the raters are better at this operating point ($p<10^{-4}$).

In summary, at high sensitivity point, algorithms' sensitivities are not indistinguishable from raters' but specificities are significantly lower.

1.4 Evaluating the Algorithms

The algorithms when run on a scan produces a list of 9 real valued confidence scores in the range of [0, 1] indicating the presence of the following findings: Intracranial hemorrhage and each of the 5 types of hemorrhages, midline shift, mass effect and calvarial fracture. As described before, the corresponding gold standards were obtained using majority voting for CQ500 dataset and by NLP algorithm of reports for Qure25k dataset. Table 3 shows AUCs of the algorithms on CQ500 dataset when a single rater is considered the gold standard and when the majority vote is considered the gold standard and Table 4 shows sensitivities and specificities of the raters versus their majority vote on CQ500 dataset.

TABLE 3

AUCs of the algorithms on CQ500 dataset when a single rater is considered the gold standard and when the majority vote is considered the gold standard.

| | Gold standard | | | |
| --- | --- | --- | --- | --- |
| Finding | Rater 1 | Rater 2 | Rater 3 | Majority Vote |
| Intracranial hemorrhage | 0.9080 | 0.9413 | 0.9356 | 0.9419 |
| Intraparenchymal | 0.9236 | 0.9430 | 0.9275 | 0.9544 |
| Intraventricular | 0.9416 | 0.9211 | 0.9364 | 0.9310 |
| Subdural | 0.8847 | 0.8957 | 0.9374 | 0.9521 |
| Extradural | 0.9049 | 0.8343 | 0.9769 | 0.9731 |
| Subarachnoid | 0.9270 | 0.9507 | 0.8975 | 0.9574 |
| Calvarial fracture | 0.9198 | 0.8653 | 0.9523 | 0.9624 |
| Mass Effect | 0.8617 | 0.9310 | 0.8850 | 0.9216 |
| Midline shift | 0.9545 | 0.9386 | 0.9461 | 0.9697 |

TABLE 4

Sensitivities and specificities of the raters versus their majority vote on CQ500 dataset.

| | Rater 1 | | Rater 2 | | Rater 3 | |
| --- | --- | --- | --- | --- | --- | --- |
| Finding | Sensitivity | Specificity | Sensitivity | Specificity | Sensitivity | Specificity |
| Intracranial hemorrhage | 0.9805 | 0.8986 | 0.9268 | 0.9790 | 0.9122 | 0.9790 |
| Intraparenchymal | 0.9552 | 0.9580 | 0.9403 | 0.9608 | 0.8955 | 0.9720 |
| Intraventricular | 0.9643 | 0.9741 | 0.9286 | 0.9914 | 0.8214 | 0.9935 |
| Subdural | 0.9245 | 0.9247 | 0.7547 | 0.9795 | 0.8113 | 0.9954 |
| Extradural | 0.6154 | 0.9958 | 0.9231 | 0.9895 | 0.9231 | 0.9979 |
| Subarachnoid | 0.9167 | 0.9722 | 0.8000 | 0.9884 | 0.9167 | 0.9466 |
| Calvarial fracture | 1.0000 | 0.9519 | 0.9519 | 0.9628 | 0.4118 | 0.9978 |
| Mass Effect | 0.9606 | 0.9148 | 0.8031 | 0.9835 | 0.9055 | 0.9560 |
| Midline shift | 0.8769 | 0.9883 | 0.9385 | 0.9038 | 0.8000 | 0.9883 |

For both CQ500 and Qure25k datasets, receiver operating characteristic (ROC) curves were obtained for each of the above by varying the threshold and plotting true positive rate (i.e. sensitivity) and false positive rate (i.e. 1-specificity) at each threshold. Two operating points were chosen on the ROC curve so that sensitivity≈0.9 (high sensitivity point) and specificity≈0.9 (high specificity 141 point) respectively. High sensitivity operating point with sensitivity closest to 0.95 was chosen. If specificity >0.7 at this operating point, this operating point was used. Otherwise, an operating point whose sensitivity is just above 0.90 if available, else the closest to 0.90, was chosen. High specificity operating point whose specificity is closest to 0.95 was chosen. If sensitivity >0.70 at this operating point, this operating point was used. Otherwise, an operating point whose specificity is just above 0.90 if available, else the closest to 0.90 was used. Areas under the ROC curve (AUCs) and sensitivities & specificities at these two operating points were used to evaluate the algorithms.

1.5 Statistical Analysis

Sample sizes for proportions and AUCs were calculated using normal approximation and the method 146 outlined by Hanley and McNeil (*Radiology*, 143(1):29-36, 1982) respectively. The prevalence of our target abnormalities in a randomly selected sample of CT scans tend to be low. This means that establishing the algorithms' sensitivity with a reasonably high confidence on an un-enriched dataset would require very large sample sizes. For example, to establish a sensitivity with an expected value of 0.7 within a 95% confidence interval of half-length of 0.10, number of positive scans to be read≈80. Similarly, for a finding with prevalence rate of 1%, to establish AUC within a 95% confidence interval of half-length of 0.05, number of scans to be read≈20000.

The Qure25k dataset used in this study was randomly sampled from the population distribution and had number of scans >20000 following the above sample size calculations. However, constraints on 155 the radiologist time necessitated the enrichment strategy outlined in the section 2.1 for the CQ500 dataset. Manual curation of scans (by referring to the scans themselves) would have had selection bias towards more significant positive scans. This issue was mitigated by random selection where positive scans were determined from the clinical reports.

Confusion matrices were generated for each finding at the selected operating points. See Table 5. The 95% confidence intervals for sensitivity and specificity were calculated from these matrices using 'exact' Clopper-Pearson method based on Beta distribution. Confidence intervals of AUCs were calculated following the 'distribution-based' approach described by Hanley and McNeil (*Radiology*, 143(1):29-36, 1982). On the CQ500 dataset, the concordance between paired raters on each finding was measured using percentage of agreement and the Cohen's kappa ($\kappa$) statistic (Viera et al. Fam Med, 37(5):360-363, 2005). In addition, concordance between all the three raters on each finding was measured using Fleiss' kappa ($\kappa$) statistic (Fleiss, et al, Statistical methods for rates and proportions. 364 John Wiley & Sons, 2013).

TABLE 5

Confusion between classes: Each row in these tables represents AUCs computed on subset of scans for which a finding is positive. For example, SDH row represents AUCs of different findings on the scans which have a SDH. A low value in EDH column of the SDH row means that algorithms do not detect EDH well if SDH is present in the scan. (ICH - SAH are intracranial hemorrhages and its subtypes, Frac is calvarial fracture, ME and MLS are mass effect and midline shift respectively.)

|     | ICH  | IPH  | IVH  | SDH  | EDH  | SAH  | Frac | ME   | MLS  |
|-----|------|------|------|------|------|------|------|------|------|
| ICH | —    | 0.80 | 0.92 | 0.87 | 0.90 | 0.80 | 0.88 | 0.82 | 0.87 |
| IPH | —    | —    | 0.92 | 0.88 | 0.91 | 0.81 | 0.89 | 0.83 | 0.86 |
| IVH | —    | 0.79 | —    | 0.94 | 0.94 | 0.80 | 0.97 | 0.79 | 0.83 |
| SDH | —    | 0.78 | 0.81 | —    | 0.73 | 0.78 | 0.83 | 0.80 | 0.85 |
| EDH | —    | 0.79 | 0.83 | 0.78 | —    | 0.77 | 0.72 | 0.71 | 0.77 |
| SAH | —    | 0.74 | 0.92 | 0.82 | 0.85 | —    | 0.85 | 0.77 | 0.84 |
| Frac| 0.87 | 0.81 | 0.90 | 0.81 | 0.86 | 0.80 | —    | 0.78 | 0.84 |
| ME  | 0.92 | 0.90 | 0.92 | 0.93 | 0.91 | 0.84 | 0.94 | —    | 0.79 |
| MLS | 0.88 | 0.87 | 0.92 | 0.95 | 0.90 | 0.80 | 0.93 | —    | —    |

(a) Qure25k dataset

|     | ICH  | IPH  | IVH  | SDH  | EDH  | SAH  | Frac | ME   | MLS  |
|-----|------|------|------|------|------|------|------|------|------|
| ICH | —    | 0.92 | 0.90 | 0.94 | 0.97 | 0.93 | 0.95 | 0.86 | 0.92 |
| IPH | —    | —    | 0.88 | 0.95 | 0.96 | 0.95 | 0.93 | 0.83 | 0.88 |
| IVH | —    | 0.99 | —    | 1.00 | 1.00 | 0.98 | 1.00 | 0.69 | 0.69 |
| SDH | —    | 0.99 | 0.84 | —    | 0.95 | 0.98 | 0.97 | 0.89 | 0.98 |
| EDH | —    | 0.79 | 0.88 | 0.83 | —    | 0.71 | 1.00 | 0.92 | 1.00 |
| SAH | —    | 0.87 | 0.87 | 0.89 | 0.94 | —    | 0.91 | 0.94 | 0.89 |
| Frac| 0.91 | 0.81 | 0.86 | 0.89 | 0.90 | 0.88 | —    | 0.84 | 0.97 |
| ME  | 0.75 | 0.94 | 0.88 | 0.97 | 0.98 | 0.94 | 0.96 | —    | 0.86 |
| MLS | 0.84 | 0.98 | 0.90 | 0.98 | 0.96 | 0.94 | 0.98 | —    | —    |

(b) Qure25k dataset

1.6. Results

Patient demographics and prevalence for each finding are summarized in Table 6. Qure25k dataset contained 21095 scans of which number of scans reported positive for intracranial hemorrhage and calvarial fracture are 2495 and 992 respectively. CQ500 dataset included 491 scans of which batch B1 had 214 scans and batch B2 had 277 scans. B1 contained 35 and 6 scans reported with intracranial hemorrhage and calvarial fracture respectively. The same for B2 were 170 and 28 respectively.

TABLE 6

Dataset characteristics for CQ500 and Qure25K datasets.

| Characteristic | Qure25K dataset | CQ500 dataset batch B1 | CQ500 dataset batch B2 |
|---|---|---|---|
| No. of scans | 21095 | 214 | 277 |
| No. of raters per scan | 1 | 3 | 3 |
| PATIENT DEMOGRAPHICS | | | |
| Age | | | |
| No. of scams for which age was known | 21095 | 189 | 251 |
| Mean | 43.31 | 43.40 | 51.70 |
| Standard deviation | 22.39 | 22.43 | 20.31 |
| Range | 7-99 | 7-95 | 10-96 |
| No. of females/No. of scans for which sex | 9030/21064 | 94/214 | 84/277 |
| was known (percentage) | (42.87%) | (43.92%) | (30.31%) |
| PREVALENCE | | | |
| No. of scans (percentage) with | | | |
| Intracranial hemorrhage | 2495 (11.82%) | 35 (16.36%) | 170 (61.37%) |
| Intraparenchymal | 2013 (9.54%) | 29 (13.55%) | 105 (37.91%) |
| Intraventricular | 436 (2.07%) | 7 (3.27%) | 21 (7.58%) |
| Subdural | 554 (2.63%) | 9 (4.21%) | 44 (15.88%) |
| Extradural | 290 (1.37%) | 2 (0.93%) | 11 (3.97%) |
| Subarachnoid | 611 (2.90%) | 9 (4.21%) | 51 (18.41%) |
| Fractures | 1653 (7.84%) | 8 (3.74%) | 31 (11.19%) |
| Calvarial Fractures | 992 (4.70%) | 6 (2.80%) | 28 (10.11%) |
| Midline Shift | 666 (3.16%) | 18 (8.41%) | 47 (16.97%) |
| Mass Effect | 1517 (7.19%) | 28 (13.08%) | 99 (35.74%) |

Qure25k dataset and batch B1 of CQ500 dataset were expected to represent the population distribution of head CT scans. This is because Qure25k dataset was randomly sampled from a large database of head CT scans while batch B1 consisted of all the head CT scans acquired at the selected centers 180 in a month. The fact that age, sex and prevalence statistics are similar for both the datasets further supports this hypothesis. CQ500 dataset as a whole, however, is not representative of the population as batch B2 was selected for higher incidence of hemorrhages. Despite this, the performance metrics viz. AUC, sensitivity, and specificity should represent the performance on population because these metrics are prevalence independent.

Figure 2A:
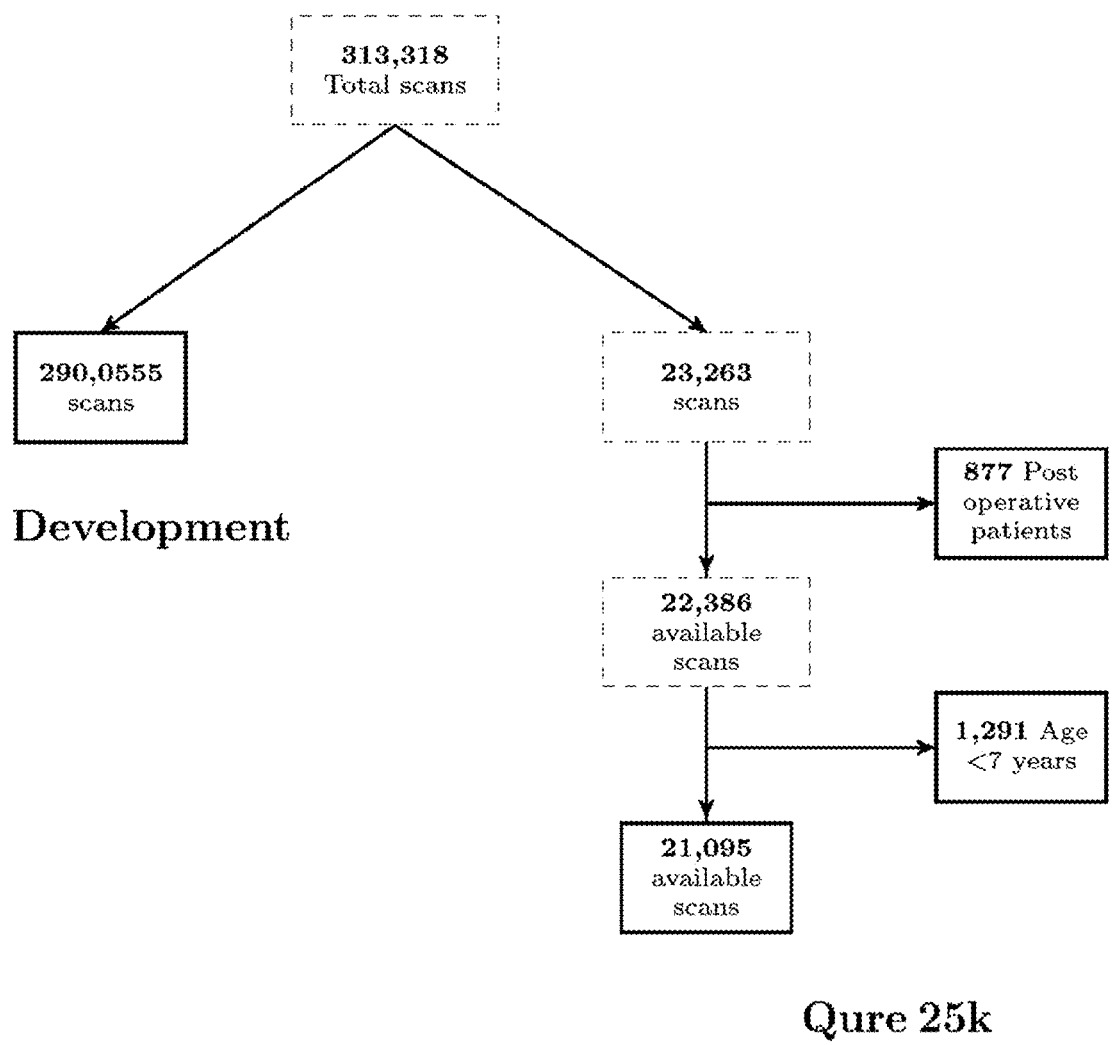
FIG. 2 Dataset section process development, Qure25k and CQ500 datasets.
Figure 2B:
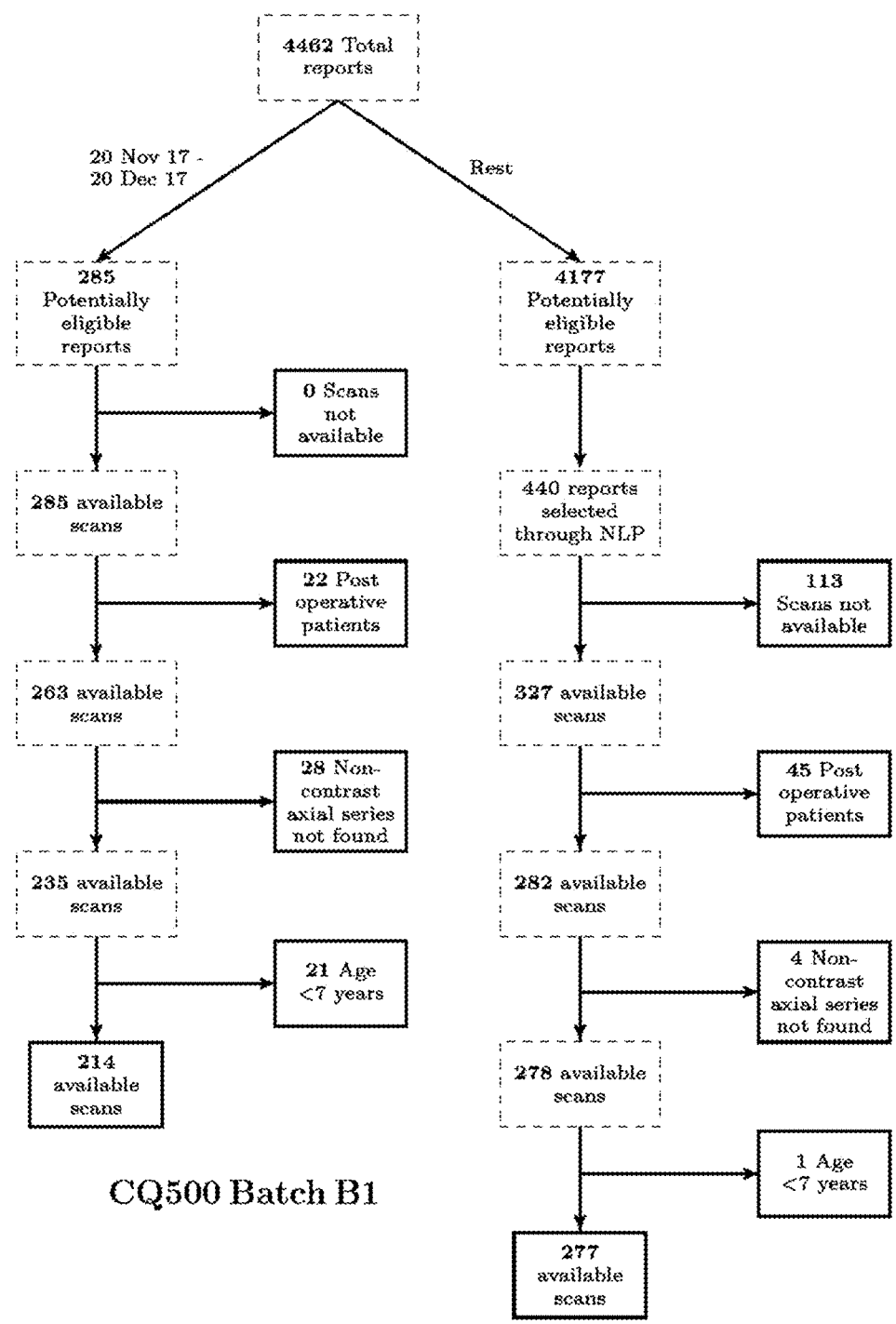

Number of clinical reports analyzed in the selection process of the CQ500 dataset was 4462. Of these, number of selected scans for batches B1 and B2 were 285 and 440 respectively. Number of exclusions were 71 and 163 respectively resulting in a total of 491 scans. Reasons for exclusion were non-availability of images (113), post-operative scans (67), scan had no non-contrast axial series (32) and patient was less than 7 years old (22). Schematic of the dataset selection process of the CQ500 dataset is presented in FIGS. 2a-2b.

1.7 Qure25K Dataset

Natural language processing (NLP) algorithm used to infer the findings from clinical reports in the Qure25k dataset was evaluated on a total of 1779 reports. Sensitivity and specificity of the NLP algorithm are fairly high; least performing finding was subdural hemorrhage with sensitivity of 0•9318 (95% CI 0•8134-0•9857) and specificity of 0•9965 (95% CI 0•9925-0•9987) while fracture was inferred perfectly with sensitivity of 1 (95% CI 0•9745-1•000) and specificity of 1 (95% CI 0•9977-1•000). Sensitivity and specificity for all the target findings on the evaluated 1779 reports is shown in Table 7a.

Table 8a and FIG. 2 summarize the performance of deep learning algorithms on the Qure25k set. Algorithm achieved AUCs of 0•9194 (95% CI 0•9119-0•9269) on intracranial hemorrhage, 0•9244 (95% CI 0.9130-0•9359) on calvarial fracture and 0.9276 (95% CI 0•9139-0•9413) on midline shift.

TABLE 7

Reliability of the gold standards for Qure25k and CQ500 datasets. On Qure25k, we used an NLP algorithm to infer findings from a radiologist's report. Three radiologists reviewed each of the 491 cases on CQ500 dataset and majority vote of the raters is used as gold standard. Table 7a shows the estimates of accuracy of the used NLP algorithm while Table 7b shows the reliability and concordance of radiologists' reads.

| Finding | Sensitivity (85% CI) | | Sensitivity (95% CI) | |
| --- | --- | --- | --- | --- |
| Intracranial hemorrhage | 203/207 | 0.9807 (0.9513-0.9947) | 1552/1572 | 0.9873 (0.9804-0.9922) |
| Intraparenchymal | 154/157 | 0.9809 (0.9452-0.9960) | 1603/1622 | 0.9883 (0.9818-0.9929) |
| Intraventricular | 44/44 | 1.0000 (0.9196-1.0000) | 1735/1735 | 1.0000 (0.9979-1.0000) |
| Subdural | 41/44 | 0.9318 (0.8134-0.9857) | 1729/1735 | 0.9965 (0.9925-0.9987) |
| Extradural | 27/27 | 1.0000 (0.8723-1.0000) | 1749/1752 | 0.9983 (0.9950-09996) |
| Subarachnoid | 51/51 | 1.0000 (0.9302-1.0000) | 1723/1728 | 0.9971 (0.993-0.9991) |
| Fractures | 143/143 | 1.0000 (0.9745-1.0000) | 1636/1636 | 1.0000 (0.9977-0.0000) |
| Calvarial Fractures | 88/89 | 0.9888 (0.9390-0.9997) | 1681/1690 | 0.9947 (0.9899-0.9976) |
| Midline Shift | 53/54 | 0.9815 (0.9011-0.9995) | 1725/1725 | 1.0000 (0.9979-1.0000) |
| Mass Effect | 129/132 | 0.9773 (0.9350-0.9953) | 1636/1647 | 0.9933 (0.9881-0.9967) |

(a) Qure25k dataset: performance of the NLP algorithm in inferring findings from the reports. This is measured on 1779 reports from the Qure25k dataset

| | Rater 1 & 2 Agreement Cohen's | | Rater 2 & 3 Agreement Cohen's | | Rater 3 & 1 Agreement Cohen's | | All Fleiss' |
| --- | --- | --- | --- | --- | --- | --- | --- |
| Finding | % | κ | % | κ | % | κ | κ |
| Intracranial hemorrhage | 89.00% (437/491) | 0.7772 | 90.84% (446/491) | 0.8084 | 88.39% (434/491) | 0.7646 | 0.7827 |
| Intraparenchymal | 91.24% (448/491) | 0.7865 | 90.63% (445/491) | 0.7651 | 90.84% (446/491) | 0.7719 | 0.7746 |
| Intraventricular | 96.13% (472/491) | 0.7042 | 97.15% (477/491) | 0.7350 | 95.72% (470/491) | 0.6550 | 0.6962 |
| Subdural | 87.98% (432/491) | 0.4853 | 93.08% (457/491) | 0.6001 | 90.02% (442/491) | 0.5624 | 0.5418 |
| Extradural | 97.35% (437/491) | 0.5058 | 98.37% (437/491) | 0.7251 | 98.17% (437/491) | 0.5995 | 0.6145 |
| Subarachnoid | 93.08% (478/491) | 0.6778 | 90.84% (483/491) | 0.6058 | 90.84% (482/491) | 0.6363 | 0.6382 |
| Calvarial Fractures | 91.85% (451/491) | 0.5771 | 92.06% (452/491) | 0.3704 | 91.24% (448/491) | 0.3637 | 0.4507 |

TABLE 7-continued

Reliability of the gold standards for Qure25k and CQ500 datasets. On Qure25k, we used an NLP algorithm to infer findings from a radiologist's report. Three radiologists reviewed each of the 491 cases on CQ500 dataset and majority vote of the raters is used as gold standard. Table 7a shows the estimates of accuracy of the used NLP algorithm while Table 7b shows the reliability and concordance of radiologists' reads.

| | | | | | | | |
|---|---|---|---|---|---|---|---|
| Midline shift | 88.19% (433/491) | 0.5804 | 87.17% (428/491) | 0.5344 | 93.69% (460/491) | 0.7036 | 0.5954 |
| Mass effect | 86.35% (423/491) | 0.6541 | 86.35% (432/491) | 0.6747 | 86.97% (427/491) | 0.6837 | 0.6698 |

(b) CQ500 dataset: concordance between the raters. Guidelines of Fleiss et al.[24] characterize κ values >0.75 as excellent agreement, 0.40-0.75 as fair to good agreement and <0.40 as poor agreement beyond chance.

TABLE 8

Performance of the algorithms on the Qure25k and CQ500 datasets. Neither of the datasets was used during the training process. AUCs are shown for 9 critical CT findings on both these datasets. Two operating points were chosen on the ROC for high sensitivity and high specificity respectively.

| Finding | AUC (95% CI) | High sensitivity operating point | | High specificity operating point | |
|---|---|---|---|---|---|
| | | Sensitivity (95% CI) | Specificity (95% CI) | Sensitivity (95% CI) | Specificity (95% CI) |
| Intracranial hemorrhage | 0.9194 (0.9119-0.9269) | 0.9006 (0.8882-0.121) | 0.7295 (0.7230-0.7358) | 0.8349 (0.8197-0.8492) | 0.9004 (0.8960-0.9047) |
| Intraparenchymal | 0.8977 (0.8884-0.9069) | 0.9031 (0.8894-0.9157) | 0.6046 (0.5976-0.6115) | 0.7670 (0.7479-0.7853) | 0.9046 (0.9003-0.9087) |
| Intraventricular | 0.9559 (0.9424-0.9694) | 0.9358 (0.9085-0.9569) | 0.8343 (0.8291-0.8393) | 0.9220 (0.8927-0.9454) | 0.9267 (0.9231-0.9302) |
| Subdural | 0.9161 (0.9001-0.9321) | 0.9152 (0.8888-0.9370) | 0.6542 (0.6476-0.6607) | 0.7960 (0.7600-0.8288) | 0.9041 (0.9000-0.9081) |
| Extradural | 0.9288 (0.9083-0.9494) | 0.9034 (0.8635-0.9349) | 0.7936 (0.7880-0.7991) | 0.8207 (0.7716-0.8631) | 0.9068 (0.9027-0.9107) |
| Subarachnoid | 0.9044 (0.8882-0.9205) | 0.9100 (0.8844-0.9315) | 0.6678 (0.6613-0.6742) | 0.7758 (0.7406-0.8083) | 0.9012 (0.8971-0.9053) |
| Calvarial fracture | 0.9244 (0.9130-0.9359) | 0.9002 (0.8798-0.9181) | 0.7749 (0.7691-0.7807) | 0.8115 (0.7857-0.8354) | 0.9020 (0.8978-0.9061) |
| Midline Shift | 0.9276 (0.9139-0.9413) | 0.9114 (0.8872-0.9319) | 0.8373 (0.8322-0.8424) | 0.8754 (0.8479-0.8995) | 0.9006 (0.8964-0.9047) |
| Mass Effect | 0.8583 (0.8462-0.8703) | 0.8622 (0.8439-0.8792) | 0.6157 (0.6089-0.6226) | 0.7086 (0.6851-0.7314) | 0.9068 (0.9026-0.9108) |

| Finding | AUC (95% CI) | High sensitivity operating point | | High specificity operating point | |
|---|---|---|---|---|---|
| | | Sensitivity (95% CI) | Specificity (95% CI) | Sensitivity (95% CI) | Specificity (95% CI) |
| Intracranial hemorrhage | 0.9419 (0.9187-0.9651) | 0.9463 (0.9060-0.9729) | 0.7098 (0.6535-0.7617) | 0.8195 (0.7599-0.8696) | 0.9021 (0.8616-0.9340) |
| Intraparenchymal | 0.9544 (0.9293-0.9795) | 0.9478 (0.8953-0.9787) | 0.8123 (0.7679-0.8515) | 0.8433 (0.7705-0.9003) | 0.9076 (0.8726-0.9355) |
| Intraventricular | 0.9310 (0.8654-0.9965) | 0.9286 (0.7650-0.9912) | 0.6652 (0.6202-0.7081) | 0.8929 (0.7177-0.9773) | 0.9028 (0.8721-0.9282) |
| Subdural | 0.9521 (0.9117-0.9925) | 0.9434 (0.8434-0.9882) | 0.7215 (0.6769-0.7630) | 0.8868 (0.7697-0.9573) | 0.9041 (0.8726-0.9300) |
| Extradural | 0.9731 (0.9113-1.0000) | 0.9231 (0.6397-0.9981) | 0.8828 (0.8506-0.9103) | 0.8462 (0.5455-0.9808) | 0.9477 (0.9238-0.9659) |
| Subarachnoid | 0.9574 (0.9214-0.9934) | 0.9167 (0.8161-0.9724) | 0.8654 (0.8295-0.8962) | 0.8667 (0.7541-0.9406) | 0.9049 (0.8732-0.9309) |
| Calvarial fracture | 0.9624 (0.9204-1.0000) | 0.9487 (0.8268-0.9937) | 0.8606 (0.8252-0.8912) | 0.8718 (0.7257-0.9570) | 0.9027 (0.8715-0.9284) |
| Midline Shift | 0.9697 (0.9403-0.9991) | 0.9385 (0.8499-0.9830) | 0.8944 (0.8612-0.9219) | 0.9077 (0.8098-0.9654) | 0.9108 (0.8796-0.9361) |
| Mass Effect | 0.9216 (0.8883-0.9548) | 0.9055 (0.8408-0.9502) | 0.7335 (0.6849-0.7782) | 0.8189 (0.7408-0.8816) | 0.9038 (0.8688-0.9321) |

(a) Qure25k dataset: the algorithms' performance
(b) CQ500 dataset: the algorithms' performance 1.8 CQ500 Dataset Concordance between the three raters on the CQ500 dataset was observed to be the highest for intracranial hemorrhage (Fleiss' κ=0•7827) and intraparenchymal hemorrhage (Fleiss' κ=0•7746), representing excellent agreement for these findings. Calvarial fracture and subdural hemorrhage had the lowest concordance with Fleiss' κ of 0•4507 and 0•5418 respectively, indicating fair to moderate agreement. For each of the target findings, percentage agreement and Cohen's kappa between a pair of raters and Fleiss' kappa for all the raters is shown in Table 8b.

Figure 3:
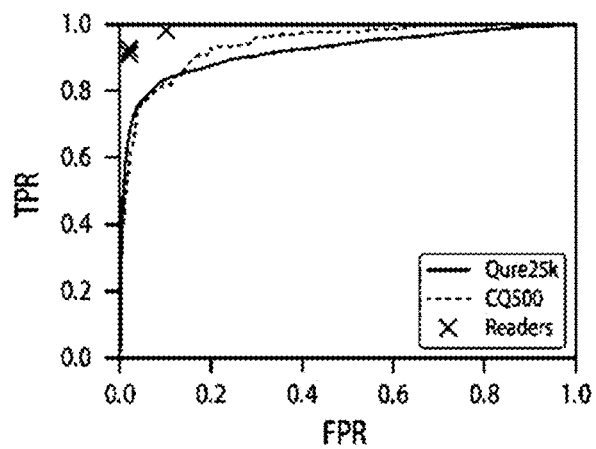
FIG. 3 Receiver operating characteristic (ROC) curves for the algorithms on Qure25k and CQ500 datasets. Blue lines are for the Qure25k dataset and Red lines are for the CQ500 dataset. Individual raters' true positive and false positive rates measured against their consensus on CQ500 dataset are also plotted along with the ROCs for comparison.
Figure 3:
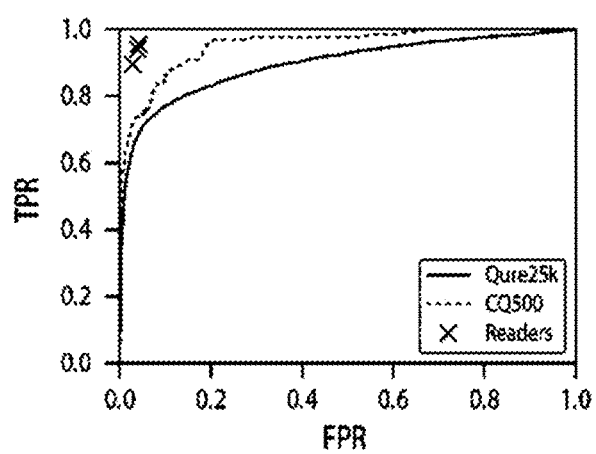
Figure 3:
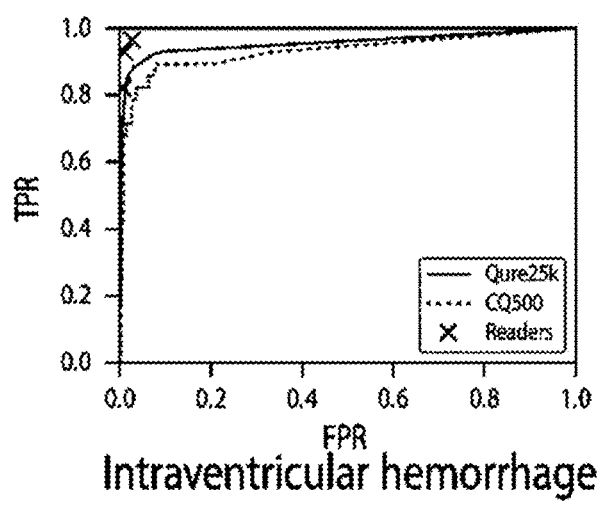
Figure 3:
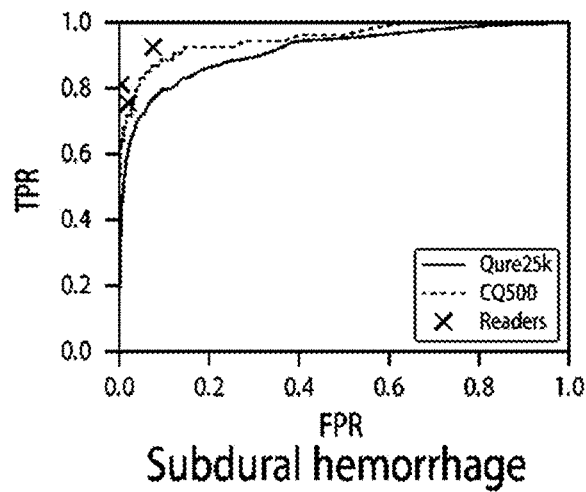
Figure 3:
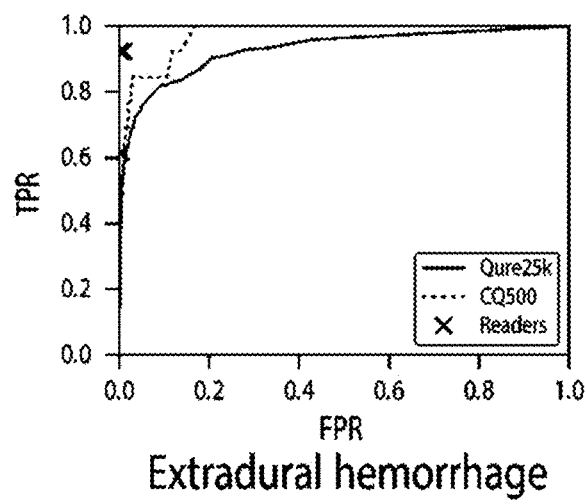
Figure 3:
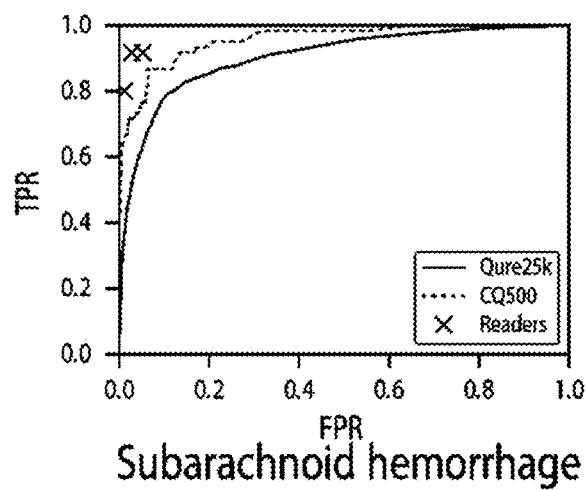
Figure 3:
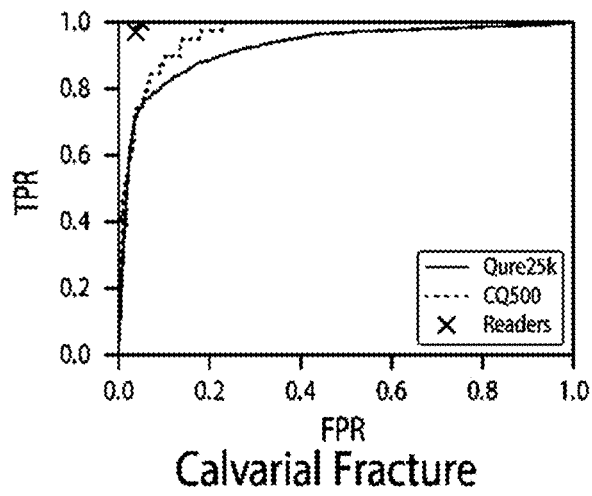
Figure 3:
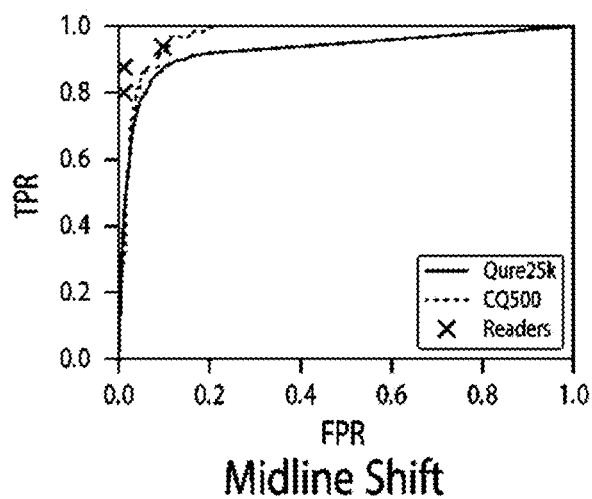
Figure 3:
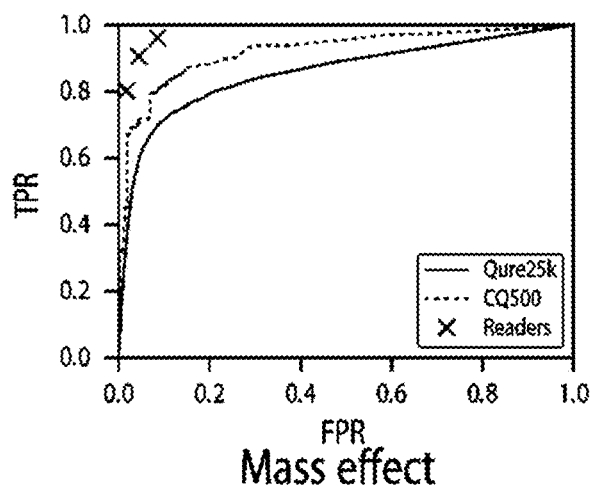

The algorithms generally performed better on the CQ500 dataset than on the Qure25k dataset. AUCs, sensitivities and specificities are shown in Table 7b and ROCs are shown in FIG. 3. AUC forintracranial hemorrhage was 0•9419 (95% CI 0•9187-0•9651), for calvarial fracture was 0•9624 (95% CI 0•9204-1•0000), and for midline shift was 0•9697 (95% CI 0•9403-0•9991).

1.9 Head CT Scan Workflow.

Figure 4:
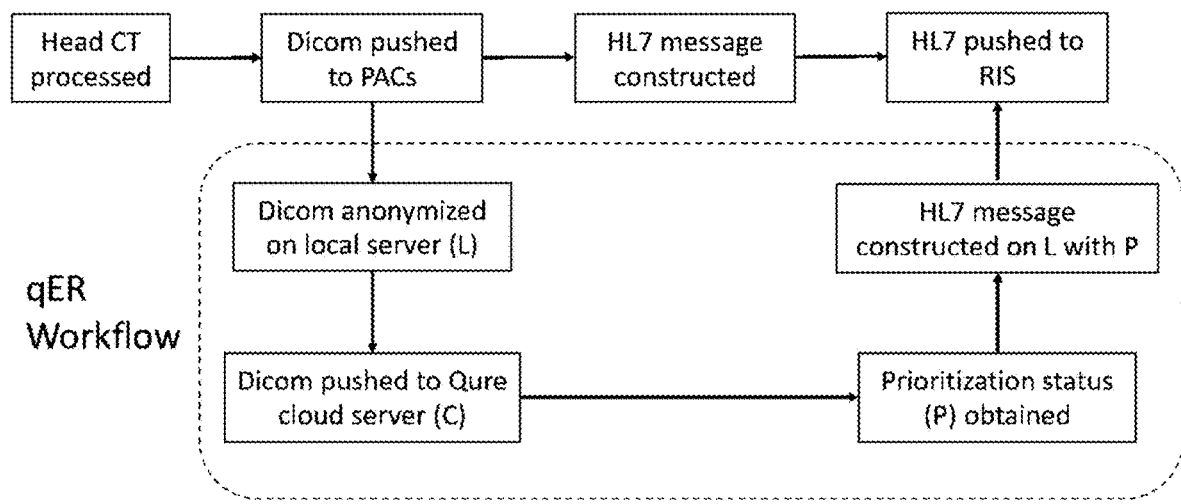
FIG. 4 Proposed workflow for head CT scan using qER.

FIG. 4 shows a proposed workflow for head CT scan using qER.

1.10 Conclusion

On Qure25k dataset, the algorithms achieved AUCs of 0•92±0•01, 0•90±0•01, 0•96±0•01, 0•92±0•02, 0•93±0•02, and 0•90±0•02 for detecting ICH, IPH, IVH, SDH, EDH and SAH respectively. AUCs for the same on CQ500 dataset were 0•94±0•02, 0•96±0•03, 0•93±0•07, 0•95±0•04, 0•97±0•06, and 0•96±0•04 respectively. For detecting calvarial fractures, midline shift and mass effect, AUCs on Qure25k dataset were 0•92±0•01, 0•93±0•01, and 0•86±0•01 respectively, while AUCs on CQ500 dataset were 0•96±0•04, 0•97±0•03, and 0•92±0•03 respectively.

The example demonstrates that deep learning algorithms can accurately identify head CT scan abnormalities requiring urgent attention. This opens up the possibility to use these algorithms to automate the triage process.

We claim:

1. A method for streamlining a head scan interpretation workflow by automating an initial screening and triage process, comprising:
    receiving and processing images from CT head scan imaging procedure data;
    detecting and localizing medical abnormalities of the images using a deep learning system,
    wherein the deep learning system carried out by a computer is developed by the steps of:
        selecting medical imaging scans and extracting the medical abnormalities using natural language processing (NLP) algorithms, wherein each type of the medical abnormalities is annotated at scan, slice and pixel levels;
        training a slice-wise deep learning algorithm with the selected medical imaging scans to segment pixel-level annotated scans;
        training the deep learning algorithm with the selected medical imaging scans to generate slice-level confidences;
        predicting confidences for a presence of each type of medical abnormalities; and
        generating a score that corresponds to a level of recognition of the medical abnormalities and outputting a mask representing the precise location and extent of the medical abnormalities; and
    prioritizing an assignment of a medical evaluation to an evaluator based on the score generated for the images.

2. The method of claim 1, wherein the CT head scan imaging procedure data are transmitted to a Picture Archiving and Communication System (PACS) via Digital Imaging and Communications in Medicine (DICOM).

3. The method of claim 2, wherein DICOM images are anonymized on a local server.

4. The method of claim 3, wherein anonymized DICOM images are transferred to a cloud server.

5. The method of claim 4, wherein detecting and localizing medical abnormalities of the images and prioritizing the assignment of a medical evaluation to an evaluator are carried out in the cloud server to obtain a prioritization status for DICOM images.

6. The method of claim 5, wherein the prioritization status for DICOM images is transferred to the local server and a Health Level Seven (HL7) message is constructed in response to the prioritization status for DICOM images.

7. The method of claim 6, wherein the HL7 message is transmitted to a Radiology Information System (RIS).

8. The method of claim 1, wherein the deep learning algorithm comprises a convolutional neural network architecture.

9. The method of claim 8, wherein the architecture is modified by using multiple parallel fully connected layers.

10. The method of claim 1, wherein the confidences at the slice-level are combined across slices using a fully connected layer to predict a scan-level confidence for the presence and types of the medical abnormalities.

11. The method of claim 1, wherein the medical abnormalities comprise intracranial hemorrhage and each of the 5 types of intracranial hemorrhages including intraparenchymal hemorrhage (IPH), intraventricular hemorrhage (IVH), subdural intracranial hemorrhage (SDH), epidural hemorrhage (EDH), and subarachnoid hemorrhage (SAH); midline shift; mass effect; skull fractures, and calvarial fractures.

12. The method of claim 1, wherein the head CT scans are preprocessed by windowing to three separate windows.

13. The method of claim 12, wherein the three separate windows comprise brain window, bone window and subdural window.

14. The method of claim 1, wherein an accuracy of the deep learning algorithm for detecting the medical abnormalities is validated by comparing with radiologist reports.

15. The method of claim 1, wherein the medical imaging procedure data comprise image data captured by an imaging modality and order data provided from a request for a radiological image read.

16. An automated head CT scan screening and triage system for streamlining a head scan interpretation workflow, comprising:
    a deep learning system carried out by a computer to detect and localize medical abnormalities on non-contrast head CT scans, wherein the deep learning system is developed by the steps of:
    selecting medical imaging scans and extracting medical abnormalities using natural language processing (NLP) algorithms, wherein each type of the medical abnormalities is annotated at scan, slice and pixel levels;
    training a slice-wise deep learning algorithm with the selected medical imaging scans to segment pixel-level annotated scans;
    training the deep learning algorithm with the selected medical imaging scans to generate slice-level confidences;
    predicting confidences for a presence of each type of medical abnormalities; and generating a score that corresponds to a level of recognition of the medical abnormalities and outputting a mask representing the precise location and extent of the medical abnormalities;

wherein the automated head CT scan screening and triage system is configured to receive and process images from CT head scan imaging procedure data;

wherein the automated head CT scan screening and triage system is configured to detect and localize the medical abnormalities of the images using the deep learning system; and wherein the automated head CT scan screening and triage system is configured to prioritize an assignment of a medical evaluation to an evaluator based on the score generated for the images.

17. The system of claim 16, wherein the CT head scan imaging procedure data are transmitted to a Picture Archiving and Communication System (PACS) via Digital Imaging and Communications in Medicine (DICOM).

18. The system of claim 17, wherein DICOM images are anonymized on a local server.

19. The system of claim 18, wherein anonymized DICOM images are transferred to a cloud server.

20. The system of claim 19, wherein detecting and localizing medical abnormalities of the images and prioritizing the assignment of a medical evaluation to an evaluator are carried out in the cloud server to obtain a prioritization status for DICOM images.

21. The system of claim 20, wherein the prioritization status for DICOM images is transferred to the local server and a Health Level Seven (HL7) message is constructed in response to the prioritization status for DICOM images.

22. The system of claim 21, wherein the HL7 message is transmitted to a Radiology Information System (RIS).

23. The system of claim 16, wherein the deep learning algorithm comprises a convolutional neural network architecture.

24. The system of claim 23, wherein the architecture is modified by using multiple parallel fully connected layers.

25. The system of claim 16, wherein the confidences at the slice-level are combined across slices using a fully connected layer to predict the scan-level confidence for the presence and types of the medical abnormalities.

26. The system of claim 16, wherein the medical abnormalities comprise intracranial hemorrhage and each of the 5 types of intracranial hemorrhages including intraparenchymal hemorrhage (IPH), intraventricular hemorrhage (IVH), subdural intracranial hemorrhage (SDH), epidural hemorrhage (EDH), and subarachnoid hemorrhage (SAH); midline shift; mass effect; skull fractures and calvarial fractures.

27. The system of claim 16, wherein the head CT scans are preprocessed by windowing to three separate windows.

28. The system of claim 27, wherein the three separate windows comprise brain window, bone window and subdural window.

29. The system of claim 16, wherein an accuracy of the deep learning algorithm for detecting the medical abnormalities is validated by comparing with the radiologist reports.

30. The system of claim 16, wherein the medical imaging procedure data comprise image data captured by an imaging modality and order data provided from a request for a radiological image read.

* * * * *